(12) United States Patent
Gunn et al.

(10) Patent No.: US 8,518,991 B2
(45) Date of Patent: Aug. 27, 2013

(54) STRUCTURED COMPOSITIONS COMPRISING BETAINE

(75) Inventors: Euen T. Gunn, Trenton, NJ (US); Glenn A. Nystrand, Lebanon, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 814 days.

(21) Appl. No.: 11/770,810

(22) Filed: Jun. 29, 2007

(65) Prior Publication Data

US 2009/0005449 A1 Jan. 1, 2009

(51) Int. Cl.
*A61K 8/42* (2006.01)
*A61Q 19/00* (2006.01)
*A61K 9/00* (2006.01)

(52) U.S. Cl.
USPC .......................................... 514/561; 424/400

(58) Field of Classification Search
None
See application file for complete search history.

(56) References Cited

U.S. PATENT DOCUMENTS

| | | | |
|---|---|---|---|
| 4,215,064 A | 7/1980 | Lindemann et al. | |
| 4,233,192 A | 11/1980 | Lindemann et al. | |
| 4,372,869 A | 2/1983 | Lindemann et al. | |
| 4,380,637 A | 4/1983 | Lindemann et al. | |
| 4,382,036 A | 5/1983 | Lindemann et al. | |
| 4,617,414 A | 10/1986 | Lukenbach et al. | |
| 5,556,628 A | 9/1996 | Derian et al. | |
| 5,872,088 A | 2/1999 | Pucci et al. | |
| 5,888,489 A * | 3/1999 | von Mallek | 424/70.19 |
| 5,952,286 A | 9/1999 | Puvvada et al. | |
| 5,962,395 A | 10/1999 | Puvvada et al. | |
| 5,965,500 A | 10/1999 | Puvvada | |
| 6,077,816 A | 6/2000 | Puvvada et al. | |
| 6,150,312 A | 11/2000 | Puvvada et al. | |
| 6,174,846 B1 | 1/2001 | Villa | |
| 6,426,326 B1 | 7/2002 | Mitra et al. | |
| 7,022,657 B2 * | 4/2006 | Hines et al. | 510/407 |
| 2002/0010110 A1 | 1/2002 | Hayward et al. | |
| 2002/0114820 A1 * | 8/2002 | Deckers et al. | 424/401 |
| 2003/0045439 A1 | 3/2003 | Evers | |
| 2005/0020468 A1 | 1/2005 | Frantz et al. | |
| 2005/0049156 A1 * | 3/2005 | Librizzi et al. | 510/130 |
| 2006/0079420 A1 | 4/2006 | Wagner et al. | |
| 2006/0094628 A1 * | 5/2006 | Wei et al. | 510/417 |
| 2006/0252662 A1 | 11/2006 | Soffin et al. | |
| 2006/0276357 A1 | 12/2006 | Smith, III et al. | |

FOREIGN PATENT DOCUMENTS

| | | |
|---|---|---|
| EP | 1097987 | 5/2001 |
| WO | WO 99/32069 A | 7/1999 |
| WO | WO 2003/055456 A | 7/2003 |
| WO | WO 03/074021 A | 9/2003 |
| WO | WO 2006/042184 A | 4/2006 |

OTHER PUBLICATIONS

European Search Report for corresponding patent application No. 08252223.4 dated Jun. 6, 2009.
Stepan Product Bulletin, CEDAPAL® TD-403 MFLD, 2008, pp. 1-2, Stepan Company.
Degussa Product Bulletin, TEGO® Betain F 50, May 2003, pp. 1-5, Goldschmidt Personal Care.

* cited by examiner

*Primary Examiner* — David J Blanchard
*Assistant Examiner* — Garen Gotfredson

(57) ABSTRACT

Provided are structured compositions comprising an anionic surfactant, a betaine, and a branched fatty alcohol, the composition having a Yield Stress from about 1 Pascal (Pa) to about 1500 Pa, as well as methods of making and using such compositions.

7 Claims, No Drawings

STRUCTURED COMPOSITIONS COMPRISING BETAINE

FIELD OF INVENTION

The present invention relates to structured compositions comprising at least one betaine, methods of making structured compositions, and uses of such compositions in personal care products.

DESCRIPTION OF THE RELATED ART

A variety of so-called "structured" compositions for use in personal care, home care, and other consumer products are known in the art. Such structured compositions are often typified by the presence of a lamellar, surfactant-rich phase, and tend to exhibit desirable Theological and aesthetic properties, as well as, significant power to suspend functional ingredients that are not soluble in water.

Applicants have recognized that for certain end uses, including but not limited to certain personal care product applications, it would be desirable to incorporate one or more betaines into a structured system to create a composition that is not only aesthetically pleasing and/or phase-stable, but also exhibits one or more additional properties such as mildness, foaming, and/or cost-effectiveness. However, applicants have further recognized that the incorporation of betaines into structured systems tends to be problematic. In particular, applicants believe that the irregular shaped hydrophilic head group of betaines tends to make such molecules particularly difficult to stabilize in a structured composition.

In light of the above, applicants have recognized the need to develop structured compositions comprising a betaine, and methods of making such compositions.

SUMMARY OF THE INVENTION

The present invention meets the aforementioned need and overcomes the disadvantages of the prior art. In particular, applicants have discovered that one or more betaines can be combined with one or more branched fatty alcohols and one or more anionic surfactants to produce structured compositions that are phase stable.

According to one aspect, the present invention provides a composition comprising a betaine, a branched fatty alcohol, and an anionic surfactant, the composition having a Yield Stress of from about 1 Pascal (Pa) to about 1500 Pa.

According to another aspect, the present invention provides a composition comprising a betaine, a branched fatty alcohol, and an anionic surfactant, the composition having an H-B dimension of less than about 1.7.

According to yet another aspect the present invention provides personal care products comprising the compositions of the present invention.

According to one aspect, the present invention provides methods of making a structured composition comprising combining a betaine, a branched fatty alcohol, and an anionic surfactant in amounts sufficient to achieve a composition having a Yield Stress of from about 1 Pascal (Pa) to about 1500 Pa.

According to another aspect, the present invention provides methods of cleansing the human body comprising applying a structured composition of the present invention to the human body.

DESCRIPTION OF PREFERRED EMBODIMENTS

All percentages listed in this specification are percentages by weight, unless otherwise specifically mentioned.

As used herein the term "structured composition," means a composition having a Yield Stress from about 1 Pascal (Pa) to about 1500 Pa as measured via the "Yield Stress Test" described in the Test Methods below. Examples of certain preferred structured compositions include those having a Yield Stress of from about 10 Pa to about 1100 Pa, as measured by the Yield Stress Method described hereafter.

As noted above, applicants have discovered unexpectedly that structured compositions may be obtained by combining at least one betaine with at least one branched fatty alcohol and at least one anionic surfactant. Applicants have further discovered that compositions of the instant invention, according to certain embodiments have the desirable attribute that may be referred to as "heaping," i.e. the ability to recover shape rapidly and form peaks when subject to shearing, as determined by the "Degree of Heaping Test" described in the Test Methods below. Accordingly, in certain embodiments, the inventive compositions have a Hauesorff-Besicovitch Dimension (hereinafter, "H-B Dimension") that is less than about 1.7, preferably less than about 1.6, more preferably less than about 1.5, and even more preferably less than about 1.4, as measured by the Degree of Heaping Test Method described hereafter.

Any of a variety of suitable betaines may be used in the compositions of the present invention. Examples of suitable betaines include alkyl betaines; amidoalkyl betaines; amidoalkyl sultaines; amphophosphates; phosphorylated imidazolines such as phosphobetaines and pyrophosphobetaines, as well as other betaines represented by the following formula:

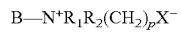

B—N$^+$R$_1$R$_2$(CH$_2$)$_p$X$^-$ wherein B is an alkyl or alkenyl group, preferably a group having from about 7 to about 22 carbon atoms; and X$^-$ is a anionically charged moiety or a neutral (protonated) derivative thereof. As will be recognized by those of skill in the art, the charge on X$^-$ may be dependent on the pH of the composition.

Examples of suitable alkyl betaines include those compounds of the formula:

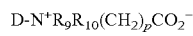

D-N$^+$R$_9$R$_{10}$(CH$_2$)$_p$CO$_2^-$ wherein
  D is an alkyl or alkenyl group having from about 8 to about 22, e.g., from about 8 to about 16 carbon atoms;
  R$_9$ and R$_{10}$ are each independently an alkyl or hydroxyalkyl group having from about 1 to about 4 carbon atoms; and
  p is 1 or 2.

A preferred betaine for use in the present invention is lauryl betaine, available commercially from Huntsman International LLC of The Woodlands, Tex., as "Empigen BB/J."

Examples of suitable amidoalkyl betaines include those compounds of the formula:

F—CO—NH(CH$_2$)$_q$—NR$^+$R$_{11}$R$_{12}$(CH$_2$)$_m$CO$_2^-$ wherein
  F is an alkyl or alkenyl group having from about 7 to about 21, e.g. from about 7 to about 15 carbon atoms;
  R$_{11}$ and R$_{12}$ are each independently an alkyl or Hydroxyalkyl group having from about 1 to about 4 carbon atoms;
  q is an integer from about 2 to about 6; and m is 1 or 2.

One amidoalkyl betaine is cocamidopropyl betaine, available commercially from Degussa Goldschmidt Chemical Corporation of Hopewell, Virginia under the tradename, "Tegobetaine L7."

Examples of suitable amidoalkyl sultaines include those compounds of the formula

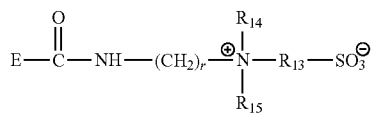

wherein
- E is an alkyl or alkenyl group having from about 7 to about 21, e.g. from about 7 to about 15 carbon atoms;
- $R_{14}$ and $R_{15}$ are each independently an alkyl, or hydroxyalkyl group having from about 1 to about 4 carbon atoms;
- r is an integer from about 2 to about 6; and
- $R_{13}$ is an alkylene or hydroxyalkylene group having from about 2 to about 3 carbon atoms;

In one embodiment, the amidoalkyl sultaine is cocamidopropyl hydroxysultaine, available commercially from Rhodia Inc. of Cranbury, N.J. under the tradename, "Mirataine CBS."

Examples of suitable amphophosphates compounds include those of the formula:

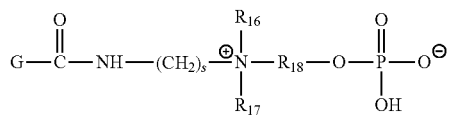

wherein
- G is an alkyl or alkenyl group having about 7 to about 21, e.g. from about 7 to about 15 carbon atoms;
- s is an integer from about 2 to about 6;
- $R_{16}$ is hydrogen or a carboxyalkyl group containing from about 2 to about 3 carbon atoms;
- $R_{17}$ is a hydroxyalkyl group containing from about 2 to about 3 carbon atoms or a group of the formula:

wherein
  - $R_{19}$ is an alkylene or hydroxyalkylene group having from about 2 to about 3 carbon atoms and t is 1 or 2; and
- $R_{18}$ is an alkylene or hydroxyalkylene group having from about 2 to about 3 carbon atoms.

In one embodiment, the amphophosphate compounds are sodium lauroampho PG-acetate phosphate, available commercially from Uniqema of Chicago, Ill. under the tradename, "Monateric 1023," and those disclosed in U.S. Pat. No. 4,380,637, which is incorporated herein by reference.

Examples of suitable phosphobetaines include those compounds of the formula:

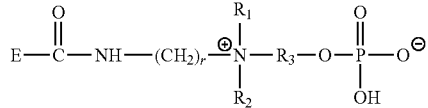

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

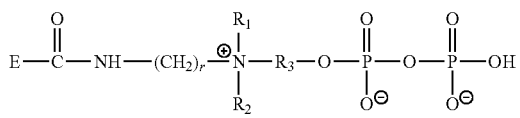

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Any amount of betaine or combination of betaines suitable, in conjunction with other ingredients in the composition, to produce a structured composition may be used in accord with the invention. According to certain embodiments, betaine is used in a concentration from greater than about 0.1% to about 50% by weight of active betaine in the composition. Preferably, betaine is in present in a concentration from about 1% to about 40%, more preferably from about 5% to about 40%, even more preferably from about 15% to about 35% of active betaine in the composition.

Any of a variety of branched fatty alcohols may be used in the present compositions. By "branched fatty alcohol", it is meant, any of various alcohols derived from plant or animal oils and fats having at least one pendant hydrocarbon-comprising chain. The branched fatty alcohol may comprise any number of carbon atoms, preferably from about 7 to about 22 carbon atoms, more preferably about 9 to about 15 carbon atoms, and even more preferably about 11 to about 15 carbon atoms. Suitable branched fatty alcohols may comprise one or more alcohol groups per molecule. In certain preferred embodiments, the fatty alcohol comprises one alcohol group per molecule.

Suitable branched fatty alcohols may comprise one or more branches in the carbon backbone of the molecule. In certain preferred embodiments, the branched fatty alcohol is monobranched. By "monobranched", it is meant the fatty alcohol has an alkyl chain with one (CH) functional group resulting in one branch in the alkyl chain, i.e. the fatty alcohol has one and only one carbon that has one hydrogen atom and three carbon atoms bonded thereto.

In certain preferred embodiments, the branched fatty alcohol is a primary alcohol. By "primary alcohol," it is meant no —COH group is bonded to more than one carbon atom.

In one particularly preferred embodiment, the branched fatty alcohol is both monobranched and a primary alcohol. In a more particularly preferred embodiment, the branched fatty alcohol is both monobranched and a primary alcohol and has only one alcohol group per molecule.

In certain preferred embodiments, the branched fatty alcohol consists solely of hydrogen, carbon, and oxygen atoms. The carbon-carbon bonds within the branched fatty alcohol may be saturated or unsaturated.

In one particularly preferred embodiment, the branched fatty alcohol is a monobranched primary fatty alcohol that can be represented by the following structure:

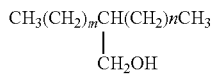

wherein each of the three following equations are satisfied: m+n=8 or 9; and m is an integer that ranges from 0 to 9 (inclusive); and n is an integer that ranges from 0 to 9 (inclusive).

Commercially available materials that are particularly suitable for use as the branched fatty alcohol include the following materials alone or in combination: Isalchem 123 or Lialchem 123 produced by Sasol Chemical Co of Bad Homburg, Germany. In a particularly preferred embodiment, the branched fatty alcohol is Isalchem 123.

In another embodiment, the branched fatty alcohol includes an alkoxylate moiety, such as ethoxy and/or propoxy groups. Any number of alkoxy groups are acceptable as long as the fatty alcohol is still capable of providing a structured composition. In one embodiment, the fatty alcohol has up to an including 10 alkoxy groups, more preferably from 0 to 3 alkoxy groups, most preferably from 1 to 3 alkoxy groups.

The concentration of the branched fatty alcohol in the composition of the invention is preferably from about 0.1% to about 10% by weight of active branched fatty alcohol in the composition, more preferably from 0.5% to about 5% by weight, even more preferably from about 0.75% to about 4%.

In one embodiment of the invention, the branched fatty alcohol and betaine are present in a fatty alcohol to betaine (weight to weight, on an actives basis) ratio that is from about 0.15:1 to about 0.35:1.

Any of a variety of suitable anionic surfactants may be used in the present invention. According to certain embodiments, suitable anionic surfactants may be branched or unbranched and may include alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain anionic surfactants include:

alkyl sulfates of the formula

alkyl ether sulfates of the formula

R'(OCH$_2$CH$_2$)$_y$OSO$_3$X';

alkyl monoglyceryl ether sulfates of the formula

alkyl monoglyceride sulfates of the formula

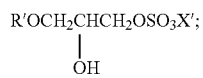

alkyl monoglyceride sulfonates of the formula

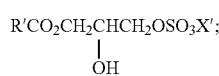

alkyl sulfonates of the formula

alkylaryl sulfonates of the formula

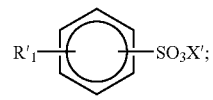

alkyl sulfosuccinates of the formula:

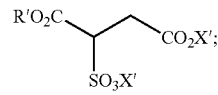

alkyl ether sulfosuccinates of the formula:

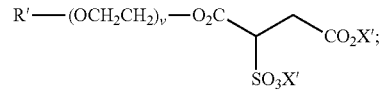

alkyl sulfosuccinamates of the formula:

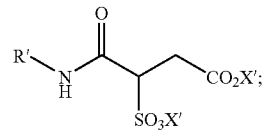

alkyl amidosulfosuccinates of the formula

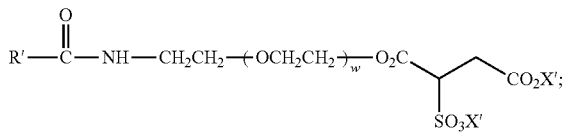

alkyl carboxylates of the formula:

R'—(OCH$_2$CH$_2$)$_w$—OCH$_2$CO$_2$X';

alkyl amidoethercarboxylates of the formula:

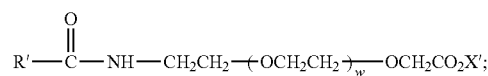

alkyl succinates of the formula:

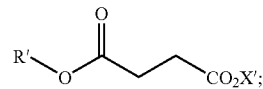

fatty acyl sarcosinates of the formula:

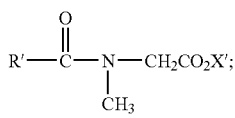

fatty acyl amino acids of the formula:

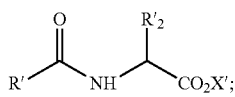

fatty acyl taurates of the formula:

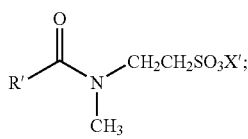

fatty alkyl sulfoacetates of the formula:

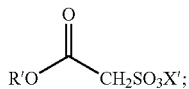

alkyl phosphates of the formula:

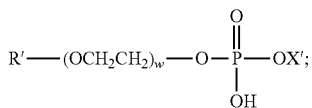

wherein

R' is an alkyl group having from about 7 to about 22, and preferably from about 7 to about 16 carbon atoms, $R'_1$ is an alkyl group having from about 1 to about 18, and preferably from about 8 to about 14 carbon atoms, $R'_2$ is a substituent of a natural or synthetic I-amino acid, X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and v is an integer from 1 to 6;

w is an integer from 0 to 20;

and mixtures thereof.

In certain preferred embodiments, the anionic surfactant for use in the present invention comprises a branched anionic surfactant. By "branched anionic surfactant," it is meant an anionic surfactant comprising more than 10% branched surfactant molecules. Suitable branched anionic surfactants include tridecanol based sulfates such as sodium trideceth sulfate, which generally comprises a high level of branching, with over 80% of surfactant molecules comprising at least 2 branches. Another suitable branched anionic surfactant is a $C_{12-13}$ alkyl sulfate derived from SAFOL 23 alcohol (Sasol, Inc, Houston, Tex., USA) which has about 15-30% branched surfactant molecules.

Branched anionic surfactants include but are not limited to the following branched anionic alkyl sulfate or alkyl ether sulfate surfactants: sodium tridecyl sulfate, sodium $C_{12-13}$ alkyl sulfate, sodium $C_{12-15}$ alkyl sulfate, sodium $C_{12-15}$ alkyl sulfate, sodium $C_{12-18}$ alkyl sulfate, sodium $C_{10-16}$ alkyl sulfate, sodium trideceth sulfate, sodium $C_{12-13}$ pareth sulfate, sodium $C_{12-13}$ pareth-n sulfate, and sodium $C_{12-14}$ pareth-n sulfate. One particularly suitable branched anionic surfactant (about 50% branched) is a sodium trideceth sulfate, available as CEDEPAL TD 430 MFLD from Stepan Company of Northfield, Ill.

Other salts of all the aforementioned branched anionic surfactants are useful, such as TEA, DEA, ammonia, potassium salts. Useful alkoxylates include the ethylene oxide, propylene oxide and EO/PO mixed alkoxylates. Phosphates, carboxylates and sulfonates prepared from branched alcohols are also useful anionic branched surfactants. Branched anoic surfactants can be derived from synthetic alcohols such as the primary alcohols from the liquid hydrocarbons produced by Fischer-Tropsch condensed syngas, for example SAFOL 23 Alcohol available from Sasol North America, Houston, Tex.; from synthetically made alcohols such as those described in U.S. Pat. No. 6,335,312 issued to Coffindaffer, et al on Jan. 1, 2002. Preferred alcohols are SAFOL.™. 23. Preferred alkoxylated alcohols are SAFOL 23-3. Sulfates can be prepared by conventional processes to high purity from a sulfur based $SO_3$ air stream process, chlorosulfonic acid process, sulfuric acid process, or Oleum process. Preparation via $SO_3$ air stream in a falling film reactor is a preferred sulfation process.

Suitable branched anionic surfactants include but are not limited to the branched anionic sulfates derived from SAFOL 23-n as previously described, where n is an integer between 1 and about 20. Fractional alkloxylation is also useful, for example by stoichiometrically adding only about 0.3 moles EO, or 1.5 moles EO, or 2.2 moles EO, based on the moles of alcohol present, since the molecular combinations that result are in fact always distributions of alkoxylates so that representation of n as an integer is merely an average representation. Preferred monomethyl branched anionic surfactants include a $C_{12-13}$ alkyl sulfate derived from the sulfation of SAFOL 23, which has about 28% branched anionic surfactant molecules.

When the branched anionic surfactant is a branched anionic primary sulfate, it may contain some of the following branched anionic surfactant molecules: 4-methyl undecyl sulfate, 5-methyl undecyl sulfate, 7-methyl undecyl sulfate, 8-methyl undecyl sulfate, 7-methyl dodecyl sulfate, 8-methyl-dodecyl sulfate, 9-methyl dodecyl sulfate, 4,5-dimethyl decyl sulfate, 6,9-dimethyl decyl sulfate, 6,9-dimethyl undecyl sulfate, 5-methyl-8-ethyl undecyl sulfate, 9-methyl undecyl sulfate, 5,6,8-trimethyl decyl sulfate, 2-methyl dodecyl sulfate, and 2-methyl undecyl sulfate. When the anionic surfactant is a primary alkoxylated sulfate, these same molecules may be present as the n=0 unreacted alcohol sulfates, in addition to the typical alkoxylated adducts that result from alkoxylation.

Any amounts of anionic surfactant or combinations thereof suitable to, in conjunction with other ingredients in the composition to produce a structured composition is suitable. According to certain embodiments, branched anionic surfactant is used in a concentration from greater than about 0.1% to about 20% by weight of active branched anionic surfactant in the composition. Preferably, branched anionic surfactant is in present in a concentration from about 0.3% to about 15%, more preferably from about 2% to about 13%, even more preferably from about 4.5% to about 10% of active branched anionic surfactant in the composition.

Additional surfactants, such as amphoteric, cationic, non-ionic, or combinations thereof may be used in compositions of the present invention. For example, any of a variety of amphoteric surfactants are suitable for use in the present invention. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants include, but are not limited to "betaines" as defined above as well as amphocarboxylates such as alkylamphoacetates (mono or di); phosphorylated imidazolines such as phosphobetaines and pyrophosphobetaines; carboxyalkyl alkyl polyamines; alkyliminodipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

wherein
A is an alkyl or alkenyl group having from about 7 to about 21, e.g. from about 10 to about 16 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or is a group of the formula:

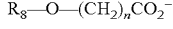

wherein
$R_8$ is an alkylene group having from about 2 to about 3 carbon atoms and n is 1 or 2; and
$R_7$ is a carboxyalkyl group containing from about 2 to about 3 carbon atoms;

Examples of suitable amphophosphate compounds include those of the formula:

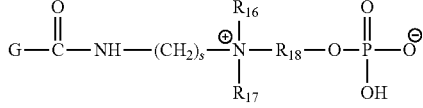

wherein
G is an alkyl or alkenyl group having about 7 to about 21, e.g. from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

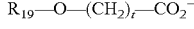

wherein
$R_{19}$ is an alkylene or hydroxyalkylene group having from about 2 to about 3 carbon atoms and t is 1 or 2; and
$R_{18}$ is an alkylene or hydroxyalkylene group having from about 2 to about 3 carbon atoms.

In one embodiment, the amphophosphate compounds are sodium lauroampho PG-acetate phosphate, available commercially from Uniqema of Chicago, Ill. under the tradename, "Monateric 1023," and those disclosed in U.S. Pat. No. 4,380,637, which is incorporated herein by reference.

Examples of suitable carboxyalkyl alkylpolyamines include those of the formula:

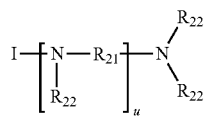

wherein
I is an alkyl or alkenyl group containing from about 8 to about 22, e.g. from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4.

In one embodiment, in order to provide a high degree of cost-effectiveness, the weight fraction of betaine relative to all amphoteric surfactants in the composition is at least about 25%, preferably at least about 50%, and most preferably at least about 75%.

Various nonionic surfactants may also be suitable. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from Uniqema of Chicago, Ill. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Cognis Corporation of Ambler, Pa. under the tradename, "Plantaren 2000."

Any amounts of nonionic surfactant suitable to produce a structured composition may be combined according to the present methods. For example, the amount of monomeric surfactants used in the present invention may be from about 2% to about 30%, more preferably from about 3% to about 25%, even more preferably from about 8% to about 20% of total active nonionic surfactant in the composition, and even more preferably from about 9% to about 15%.

Various cationic surfactants may also be suitable for use in the present compositions. Examples of suitable cationic surfactants include, but are not limited to alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

As will be recognized by those of skill in the art, the compositions of the present invention further comprise water, which serves to provide a vehicle about which a structured phase is dispersed. The concentration of water in the composition is sufficient to stabilize the composition, but not so great as to prevent the composition from becoming structured. In one embodiment, the concentration of water is from about 5% to about 70%, preferably from about 15% to about 60%, more preferably from about 20% to about 50%, and most preferably from about 25% to about 45%.

In certain embodiments of the invention, compositions of the present invention include other functional ingredients. By other functional ingredients it is meant any moiety that serves one or more functions either to stabilize or provide aesthetic benefits to the composition or to impart one or more of various benefits to the end user. These various functional ingredients may be of any form at room temperature (e.g., solids, liquids, pastes and the like) and be dispersed, emulsified, or solubilized or otherwise homogenized within the composition.

A wide variety of functional ingredients may be used in compositions of the present invention, although it is preferred that the ingredient does not adversely affect the phase stability of the composition. By "adversely effect the phase stability," it is meant that by including the particular functional ingredient, when subject to a stability challenge (e.g., held at 22° C., 50% relative humidity for a week; when subject to three 48 hour freeze-thaw cycles) the composition irrevocably phase separates into two or more visually distinct phases so as to be displeasing (e.g., in a tactile, olfactory, and/or visual sense) for topical use.

Functional ingredients that may be used include, but are in no way limited to: dyes and colorants; ultraviolet filters and sunscreens, opacificiers, matting agents, rheology modifiers, oils, emollients, and skin conditioners; chelating and sequestering agents, pH adjusters, humectants, film forming polymers, plasticizers, fragrance components; water soluble solvents such as glycols including glycerol, propylene glycol C1-C6 alcohols may be incorporated into the composition (again, as long as There is no adverse effect on phase stability) and various benefit agents, as described below.

The functional ingredient may be water-insoluble. By "water-insoluble," it is meant, a moiety that cannot be rendered essentially completely soluble in deionized water at 25° C., after providing a 1% by weight of said moiety in said deionized water under moderate agitation for 10 minutes. A wide variety of water-insoluble components may be incorporated into compositions of the present invention. The structured nature of the composition is suitable for dispersing water insoluble components that are solid at room temperature (e.g., certain polymers and waxes; dyes; and particulates such as mineral oxides, silicates, aluminosilicates, zinc pyrithione, colloidal oat flour, soy derivatives and the like) or liquid at room temperature (e.g., oils, emollients, and skin conditioners; biological actives; fragrance components).

By way of example, any of a variety of commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent may be present in an amount, based upon the total weight of the composition, of from about 1 percent to about 10 percent, e.g. from about 1.5 percent to about 7 percent or from about 2 percent to about 5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO\text{-}(JO)_a\text{---}H$, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof The pearlescent or opacifying agent may be introduced to the structured composition as a pre-formed, stabilized aqueous dispersion, such as that commercially available from Cognis Corporation of Ambler, Pa. under the tradename, "Euperlan PK-3000." This material is a combination of glycol distearate (the diester of ethylene glycol and stearic acid), Laureth-4 $(CH_3(CH_2)_{10}CH_2(OCH_2CH_2)_4OH)$ and cocamidopropyl betaine and may be in a weight percent ratio of from about 25 to about 30: about 3 to about 15: about 20 to about 25, respectively.

Any of a variety of commercially available secondary conditioners, such as volatile silicones, which impart additional attributes, such as gloss to the hair are suitable for use in this invention. The volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids. Other suitable secondary conditioners include cationic polymers, including polyquarterniums, cationic guar, and the like.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, polyglycerols, and mixtures thereof, 2)polyalkylene glycol of the formula: $HO-(R''O)_b-H$, wherein R'' is an alkylene group having from about 2 to about 3 carbon atoms and b is an integer of from about 2 to about 10; 3) polyethylene glycol ether of methyl glucose of formula $CH_3-C_6H_{10}O_5-(OCH_2CH_2)_c-OH$, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include, for example, parabens, quaternary ammonium species, phenoxyethanol, benzoates, DMDM hydantoin, and are present in the composition in an amount, based upon the total weight of the composition, from about 0 to about 1 percent or from about 0.05 percent to about 0.5 percent.

While it is typically unnecessary to include thickening agents in the composition (since the "thickening" is typically aesthetically and cost-effectively accomplished using the combination of betaine and the fatty alcohol), it is possible to incorporate any of a variety of commercially available thickening agents, which are capable of imparting the appropriate viscosity to the personal cleansing compositions are suitable for use in this invention.

Examples of suitable thickening agents nonexclusively include: mono or diesters of 1) polyethylene glycol of formula: $HO-(CH_2CH_2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; hydrophobically-modified alkali swellable emulsions (HASEs); hydrophobically-modified ethoxylated urethanes (HEURs); xantham and guar gums; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

Compositions of the present invention may include a benefit agent. A benefit agent is any element, an ion, a compound (e.g., a synthetic compound or a compound isolated from a natural source) or other chemical moiety in solid (e.g. particulate), liquid, or gaseous state and compound that has a cosmetic or therapeutic effect on the skin, hair, mucosa, or teeth. As used herein, the term "benefit agent" includes any active ingredient such as a cosmetic or pharmaceutical, that is to be delivered into and/or onto the skin, hair, mucosa, or teeth at a desired location.

The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed.

Examples of suitable benefit agents include those that provide benefits such as, but not limited to: emollients, moisturizing and water-loss prevention agents; cleansing agents; depigmentation agents; reflectants and optical modifiers; amino acids and their derivatives; antimicrobial agents; allergy inhibitors; anti-acne agents; anti-aging agents; anti-wrinkling agents, antiseptics; analgesics; shine-control agents; antipruritics; local anesthetics; anti-hair loss agents; hair growth promoting agents; hair growth inhibitor agents, antihistamines; antiinfectives; anti-inflammatory agents; anticholinergics; vasoconstrictors; vasodilators; wound healing promoters; peptides, polypeptides and proteins; deodorants and antiperspirants; medicament agents; skin firming agents, vitamins; skin lightening agents; skin darkening agents; antifungals; depilating agents; counterirritants; hemorrhoidals; insecticides; enzymes for exfoliation or other functional benefits; enzyme inhibitors; poison ivy products; poison oak products; burn products; anti-diaper rash agents; prickly heat agents; vitamins; herbal extracts; vitamin A and its derivatives; flavenoids; sensates and stress-reducing agents; anti-oxidants; hair lighteners; sunscreens; anti-edema agents, neo-collagen enhancers, anti-dandruff/sebhorreic dermatitis/psoriasis agents; keratolytics; lubricants; lightening and whitening agents; calcification, fluoridation and mineralization agents; and mixtures thereof.

The amount of the benefit agent that may be used may vary depending upon, for example, the ability of the benefit agent to penetrate through the skin, nail, mucosa, or teeth; the specific benefit agent chosen, the particular benefit desired, the sensitivity of the user to the benefit agent, the health condition, age, and skin and/or nail condition of the user, and the like. In sum, the benefit agent is used in a "safe and effective amount," which is an amount that is high enough to deliver a desired skin or nail benefit or to modify a certain condition to be treated, but is low enough to avoid serious side effects, at a reasonable risk to benefit ratio within the scope of sound medical judgment.

Compositions of the present invention are structured, i.e., have a Yield Stress from about 1 Pascal (Pa) to about 1500 Pa; more preferably from about 10 Pa to about 1100 Pa and preferably include a lamellar phase that is largely composed of one or more surfactants that is dispersed within an exterior (typically aqueous) phase. The viscosity of the personal care composition may be such that the composition is spreadable such as that of a cream or lotion or gel. For example, when measured using a LVT3 spindle at 30 rpm, the viscosity may be from about 500 cps to about 2000cps.

The pH of the present compositions is not critical, but may be in a range that does not facilitate irritation to the skin, such as from about 5 to about 7.5.

In one embodiment of the present invention the structured composition comprises at least two visually distinct phases wherein a first phase is visually distinct from a second phase. Preferably, the visually distinct phases are packaged in physical contact with one another and are stable. Preferably, the visually distinct phases form a pattern such as stripes, ribbons, or striations. The ratio of a first phase to a second phase is typically from about 1:99 to about 99:1, preferably from 90:10 to about 10:90, more preferably about from 70:30 to about 30:70, still even more preferably about 50:50. As known in the art, the first visually distinct phase may include the components in a manner sufficient to provide structure, e,g, betaine, branched anionic surfactant, and branched fatty alcohol. The second visually distinct phase may also include the above-mentioned components in a manner sufficient to provide structure. Alternatively, the second phase may be unstructured.

Compositions of the present invention are typically extrudable or dispensable from a package, such as to be applied directly or indirectly, topically or orally to the body or another surface. Depending upon the particular function, compositions of present invention may be rinsed with water or rubbed onto the skin and allowed to remain without rinsing. Preferably, the compositions of the present invention are rinse-off formulations, by which is meant the product is applied topically to the skin or hair and then subsequently (i.e., within minutes) the skin or hair is rinsed with water, or otherwise wiped off using a substrate or other suitable removal means with deposition of a portion of the composition. Particularly suitable uses for compositions of the present invention include body washes and conditioners as well as hair shampoos and conditioners, and facial cleansers. Compositions of the present invention may also be used for cleansers with acne-treatment benefit agents, stress-relief compositions (e.g. compositions with high concentrations, such as greater than about 1%, preferably greater than about 3% of fragrant compounds), among other personal care applications.

In certain embodiments, the compositions produced via the present invention are preferably used as or in personal care products for treating or cleansing at least a portion of the human body. Examples of certain preferred personal care products include various products suitable for application to the skin, hair, and/or vaginal region of the body, such as shampoos, hand, face, and/or body washes, bath additives, gels, lotions, creams, and the like. As discussed above, applicants have discovered unexpectedly that the instant methods provide cost-effective personal care products having good aesthetics, and in certain embodiments one or more of desirable properties such as foaming characteristics, rheology, foam, and high surfactant loading.

The present invention provides methods of treating and/or cleansing the human body comprising contacting at least a portion of the body with a composition of the present invention. Certain preferred methods comprising contacting mammalian skin, hair and/or vaginal region with a composition of the present invention to cleanse such region and/or treat such region for any of a variety of conditions including, but not limited to, acne, wrinkles, dermatitis, dryness, muscle pain, itch, and the like. In certain preferred embodiments, the contacting step comprises applying a composition of the present invention to human skin, hair or vaginal region.

The cleansing methods of the present invention may further comprise any of a variety of additional, optional steps associated conventionally with cleansing hair and skin including, for example, lathering, rinsing steps, and the like.

The present invention further provides methods of making a structured composition comprising a betaine comprising combining a betaine, branched fatty alcohol, and anionic surfactant. For example, one or more structured compositions comprising, consisting essentially of, or consisting of betaine, branched fatty alcohol and anionic surfactant may be combined by pouring, mixing, adding dropwise, pipetting, pumping, and the like, any one or more of such ingredients or compositions comprising such ingredients into any one or more of the other ingredients or compositions comprising such other ingredients in any order and optionally using any conventional equipment such as a mechanically stirred propeller, paddle, and the like.

The methods of the present invention may further comprise any of a variety of steps for mixing or introducing one or more of the optional components described hereinabove with or into the structured composition of the present invention either before, after, or simultaneously with the combining step described above. While in certain embodiments, the order of mixing is not critical, it is preferable, in other embodiments, to pre-blend certain components, such as the fragrance and the nonionic surfactant before adding such components into the structured composition.

EXAMPLES

The following Yield Stress Test is used in the instant methods and in the following Examples. In particular, as described above, the Yield Stress test is used to determine whether a composition is structured, according to the present invention. Furthermore, the Degree of Heaping Test is used to determine the ability of the composition to recover shape rapidly.

Yield Stress Test:

The following Yield Stress Test was performed on various personal care compositions to determine the Yield Stress according to the present invention. Samples were placed in a water bath set at 25° C. for a period time sufficient to allow the sample to equilibrate (at least about an hour). The procedure was accomplished by gently placing about 1.0 grams of the composition to be tested was on the base plate of a properly calibrated rheometer (e.g., Advanced Rheometer AR 2000) having a 20 mm cone with a 1 degree angle, a 20 mm plate, a water bath, and a solvent trap. The sample size was just sufficient to allow some minor flow of the sample out of the gap once the final position of the cone and plate was reached (0.030 mm). To minimize shearing of the sample prior to testing, each sample was applied to the plate in a consistent manner, by gently scooping out the sample in one motion without significant shear or spreading, evenly layered on the plate, and without compressing and rotating the spatula away from the sample. The sample was centered on the base plate and laid relatively even across the plate. Once the measurement position was reached, a small bulge of the sample material protruded from the gap. This was removed quickly and gently so as not to disturb the top plate and pre-shear the sample. [If the top plate was moved then the run was aborted.] The sample preparation described thus far was less than 20 seconds to reduce undue drying of the sample. The instrument was set for a controlled shear rate run (log) with a shear rate spanning from $0.01^{-1}$, to $300^{-1}$; 300 data points collected; 300 seconds test duration; 25° C. water bath. The output device attached to the rheometer was set to plot stress (Pa) as a function of shear rate $s^{-1}$. Yield stress was determined from the plot of yield stress versus shear rate as the stress at which the curve departs from linearity. The average and standard deviation of the 3 runs was determined.

Degree of Heaping Test:

The following Degree of Heaping Test was performed on various personal care compositions to determine the H-B Dimension according to the present invention.

Immediately after completing the Yield Stress Test above, the cone was then removed from the plate using the automated lift motor on the rheometer. The sample was left on the plate for 30 minutes and a digital picture was taken with a Canon S25, 5 megapixel camera. The picture is evaluated using a box counting technique method, starting with a box scale of one box covering the plate sample area and doubling the number of boxes with each iteration until the number of boxes equals one thousand and twenty four. The H-B dimension of the material is calculated by plotting log N(1) versus log 1, where N(1) is a number of boxes containing any surface of the material and 1 is a resolution representing the reciprocal of the number of the boxes (i.e., box resolution) and wherein the H-B dimension is a straight line slope of the plot from eight boxes to one thousand and twenty four boxes. The test method repeated so that 10 replicates were performed for each sample. If the resulting H-B dimension has a relative standard deviation of less than 10% the value is reported for the sample.

Examples Ex.1-Ex.3

Preparation of Inventive Examples

The inventive structured compositions of Examples Ex. 1 through Ex.3 were prepared by blending a particular ingredient with other ingredients according to the materials and amounts listed in Table 1:

TABLE 1

| | | Concentration (wt %) | | |
|---|---|---|---|---|
| Trade Ingredient | INCI Name | Ex. 1 | Ex. 2 | Ex. 3 |
| Deionized Water | Water | 38.00 | 37.00 | 36.00 |
| Cedepal TD 430 MFLD | Sodium Trideceth Sulfate | 30.00 | 30.00 | 30.00 |
| Tegobetaine L7V | Cocamidopropyl Betaine | 30.00 | 30.00 | 30.00 |
| Isalchem 123A | C12-13 Alcohols | 2.00 | 3.00 | 4.00 |
| Viscosity (cps) | | 1664 | 920 | 652 |

The structured compositions noted in Table 1 were prepared as follows: Ingredients were added in the order listed to a suitable size vessel equipped with an overhead propeller type mixer. Agitation was sufficient to maintain good batch movement without aeration. Components were added while maintaining constant agitation. pH was measured after the last component was added and adjusted to 5.5-6.5 Citric acid was then added to reduce to pH to between about 5.7. Specifically 0.12%, 0.11%, and 0.10% of citric acid was added to Ex. 1, Ex. 2, and Ex. 3 respectively to reduce the pH to 5.70, 5,70 and 5.74 respectively. Examples Ex. 1-Ex.3 were evaluated for viscosity using a standard Brookfield DV–I+viscometer with rotating LVT3 spindle at 30 rpm, with values in centipoise (cps) reported in Table 1.

Examples Ex. 4-Ex. 7

Preparation of Inventive Examples

The inventive structured compositions of Examples Ex.4 through Ex.7 were prepared by blending a particular ingredient with other ingredients according to the materials and amounts listed in Table 1:

TABLE 2

| | | Concentration (wt. %) | | | |
|---|---|---|---|---|---|
| Trade Ingredient | INCI Name | Ex. 4 | Ex. 5 | Ex. 6 | Ex. 7 |
| Deionized Water | Water | 36.00 | 33.00 | 36.00 | 33.00 |
| Cedepal TD 430 MFLD | Sodium Trideceth Sulfate | 30.00 | 30.00 | 30.00 | 30.00 |
| Tegobetaine L7V | Cocamidopropyl Betaine | 30.00 | 30.00 | 30.00 | 30.00 |
| Isalchem 123A | C12-13 Alcohols | 2.00 | 2.00 | 2.00 | 2.00 |
| Avena-Lipid | Avena sativa (Oat) Kernel Oil | 2.00 | 5.00 | — | — |
| Snow White Petrolatum, USP | Petrolatum | — | — | 2.00 | 5.00 |
| Viscosity | | 3304 | — | 1620 | 2040 |

The structured compositions noted in Table 2 were prepared in a manner similar to Ex. 1-Ex. 3: Ingredients were added in the order listed to a suitable size vessel equipped with an overhead propeller type mixer. Agitation was sufficient to maintain good batch movement without aeration. Components were added while maintaining constant agitation. Examples 6 & 7 were heated to 40-50 C to facilitate liquification of the petrolatum and confirm that the batch was homogeneous. Heating was stopped and the batch was allowed to cool to ambient room temperature while maintaining agitation during the cooling phase. pH was measured after the last component was added and adjusted to 5.5-6.5 Citric acid was then added to reduce to pH to between about 5.7. Specifically 0.12%, 0.15%, 0.13%, and 0.15% of citric acid was added to Ex. 4, Ex. 5, Ex. 6 and Ex. 7 respectively to reduce the pH to 5.65, 5,55, 5.53, and 5.60 respectively. Examples Ex.4-Ex.7 were evaluated for viscosity using a LVT3 spindle at 30rpm, with values in centipoises (cps) reported in Table 2. Example 5 was not evaluated for viscosity since it was too viscous to give a reliable viscosity reading using the viscometer.

Examples Exs. 8 and 9 and Comparative Examples C1 and C2

Preparation of Examples and Comparative Structuring Efficiency

The inventive structured compositions of Examples Ex.8 and Ex. 9, and comparative Examples C1 and C2, were prepared by blending ingredients according to the materials and amounts listed in Tables 3 and 4:

TABLE 3

| | | Concentration Wt. % | |
|---|---|---|---|
| Trade Ingredient | INCI Name | Ex. 8 | C1 |
| Deionized Water | Water | 33.00 | 33.00 |
| Cedepal TD 430 MFLD | Sodium Trideceth Sulfate | 30.00 | 30.00 |
| Tegobetaine L7V | Cocamidopropyl Betaine | 30.00 | 30.00 |
| Isalchem 123A | C12-13 Alcohols | 2.00 | |
| C12-14 Alcohol | Lauryl Alcohol | | 2.00 |
| Avena-Lipid | Avena sativa (Oat) Kernel Oil | 5.00 | 5.00 |
| | | 100.00 | 100.00 |
| | pH unadjusted | 6.46 | 6.45 |

TABLE 4

| | | Concentration Wt. % | |
|---|---|---|---|
| Trade Ingredient | INCI Name | Ex. 9 | C2 |
| Deionized Water | Water | 33.00 | 33.00 |
| Cedepal TD 430 MFLD | Sodium Trideceth Sulfate | 30.00 | 30.00 |
| Tegobetaine L7V | Cocamidopropyl Betaine | 30.00 | 30.00 |
| Isalchem 123A | C12-13 Alcohols | 2.00 | |
| C12-14 Alcohol | Lauryl Alcohol | | 2.00 |
| Avena-Lipid | Avena sativa (Oat) Kernel Oil | 5.00 | 5.00 |
| | | 100.00 | 100.00 |
| | pH adjusted | 5.76 | 5.65 |
| | grams of citric acid required to lower pH of 100 grams of base | 0.1 | 0.06 |

Two experiments were conducted to compare the structuring efficiency of the branched C12-13 Alcohols to Lauryl Alcohol, a straight chain alcohol. Processes used are comparable to those described previously. Compositions 8 and C1 were prepared and aged in glass jars at ambient temperature conditions for 4 days. Example 8 maintained good physical stability without visual phase separation whereas example C1 demonstrated visual phase instability (separation into two distinct layers) after storage for the same period. Compositions Ex. 9 and C2 were prepared and aged in glass jars at 50C for 4 days. Example 9 maintained good physical stability without visual phase separation whereas example C2 demonstrated visual phase instability (separation into two distinct layers) after storage for the same period.

Examples Exs. 1 and 3 and Comparative Example C3

Preparation of Comparative Example and Comparative Structuring Efficiency

The preparation of Inventive Examples Ex. 1 and Ex.3 are described above. Comparative Example C3 was prepared by blending ingredients according to the materials and amounts listed in Table 5:

TABLE 5

| Trade Ingredient | INCI Name | Concentration (wt %) C3 |
| --- | --- | --- |
| Deionized Water | Water | 71.70 |
| Cedepal TD 430 MFLD | Sodium Trideceth Sulfate | 9.00 |
| Tegobetaine L7V | Cocamidopropyl Betaine | 13.00 |
| PEG 80 Sorbitan Laurate | Pethylene glycol 80 - Sorbitan Laurate | 5.00 |
| PEG 6000 | Pethylene glycol 6000 | 1.00 |
| NaCl | NaCl | 0.3 |

Five experiments were conducted to compare the structuring efficiency of the inventive examples to a conventional non-structured system. Processes used are comparable to those described previously. Compositions Ex. 1 and Ex. 3 were evaluated according to the Yield Stress Test. Compositions Ex. 1, Ex. 3, and C3 were evaluated according to the Degree of Heaping Test. Results for Yield Stress, Yield Stress standard deviation and H-B Dimension are reported in Table 6:

TABLE 6

|  | Ex. 1 | Ex. 3 | C3 |
| --- | --- | --- | --- |
| Yield Stress (Pa) | 47 | 23 | — |
| Std. Dev (Pa) | 1.6 | 2.2 |  |
| H-B Dimension | 1.36 | 1.51 | 1.96 |

Examples Ex. 1 and Ex. 3 showed structuring, as evidenced by both Yield Stress and H-B dimension, whereas example C3 demonstrated no structuring. Yield stress was not evaluated for example C3.

Examples Ex. 10

Preparation of inventive Example and Structuring Efficiency

The inventive structured compositions of Examples Ex. 10 was prepared by blending a particular ingredient with other ingredients according to the materials and amounts listed in Table 7:

TABLE 7

| Trade Ingredient | INCI Name | Concentration (wt %) Ex. 10 |
| --- | --- | --- |
| Deionized Water | Water | 21.10 |
| Mackol CAS 100N | Sodium Coco-Sulfate | 1.00 |
| Tegobetaine L7V (32% active) | Cocamidopropyl Betaine | 32.00 |
| Jaguar C17 | Guar Hydroxypropyltrimonium Chloride | 0.50 |
| Versene NA | Disodium EDTA | 0.20 |
| Miranol Ultra L 32 (32% active) | Sodium Lauroamphoacetate | 4.00 |
| Cedepal TD 430 MFLD (31%) | Sodium Trideceth Sulfate | 28.00 |
| Isalchem 123A | C12-13 Alcohols | 2.00 |
| Dow Corning 200 Fluid (60,000 cSt) | Dimethicone | 0.75 |
| Merquat 550 | Polyquaternium-7 | 1.00 |
| Sunflower Oil | Helianthus Annuus (Sunflower) Seed Oil | 3.00 |
| White Petrolatum | Petrolatum | 1.00 |
| Lurury Fragrance 475537 | Fragrance | 4.00 |
| Colloidal Oat Flour 11615 | Avena sativa (Oat) Kernal Flour | 0.50 |
| Mackstat DM | DMDM Hydantoin | 0.45 |
| Citric Acid 50% | Citric Acid | 0.5 |

The structured composition noted in Table 7 was prepared as follows: Sodium coco-sulfate was pre-mixed with sufficient water in a suitable size vessel equipped with an overhead propeller type mixer. Agitation was sufficient to maintain good batch movement without aeration. The coco-sulfate was mixed until homogeneous, with the temperature adjusted to from about 40° C. to about 50° C. The heat source was removed and a premix of guar hydroxypropyltrimonium chloride in about 4.0% of the total water of the formulation was added to the coco-sulfate and allowed to mix for 15-30 minutes. A premix of Avena sativa also in about 4.0% of the total water of the formulation was then added and allowed to mix for 15-30 minutes. Cocoamidipropyl betaine, EDTA, amphoacetate, and then the remaining ingredients were added in the order listed. pH was measured after the last component was added and adjusted to 5.5-6.5. Ex. 10 was placed at 50C for 4 weeks and surprisingly remained phase stable despite a high level of emollient oils (4.75% including the dimethicone, sunflower oil, petrolatum) and fragrance oil (4.0%).

Examples Ex. 11

Preparation of Inventive Example

The inventive structured composition of Example Ex.11 was prepared by blending a particular ingredient with other ingredients according to the materials and amounts listed in Table 8:

TABLE 8

| Trade Ingredient | INCI Name | Concentration (wt %) Ex. 11 |
| --- | --- | --- |
| Deionized Water | Water | 41.55 |
| Mackol CAS 100N | Sodium Coco-Sulfate | 1.00 |
| Tegobetaine L7V (32% active) | Cocamidopropyl Betaine | 12.50 |
| Miranol Ultra L 32 (32% active) | Sodium Lauroamphoacetate | 4.00 |

TABLE 8-continued

| Trade Ingredient | INCI Name | Concentration (wt %) Ex. 11 |
|---|---|---|
| Cedepal TD 430 MFLD (31%) | Sodium Trideceth Sulfate | 28.00 |
| Isalchem 123A | C12-13 Alcohols | 2.00 |
| Other* | — | 10.95 |

*Chelating agents, fragrance, pH adjusters, humectants, emollient oils and other water insolubles The structured composition noted in Table 8 was prepared in a manner similar to that described above for Ex. 10.

We claim:

1. A composition comprising from 5% to about 40% active betaine selected from the group consisting of amidoalkyl betaines, amidoalkyl sultaines, and combinations of two or more thereof, a branched fatty alcohol represented by the formula:

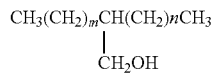

wherein m is an integer from 0 to 9 inclusive, n is an integer from 0 to 9 inclusive, and m+n=8 or 9, and from about 2 to about 13% active branched anionic surfactant, said composition comprising a lamellar phase and having an H-B dimension of less than 1.7.

2. The composition of claim 1, wherein said anionic surfactant is selected from the group consisting of a tridecyl sulfate, sodium $C_{12-13}$ alkyl sulfate, a $C_{12-15}$ alkyl sulfate, sodium $C_{12-18}$ alkyl sulfate, a $C_{10-16}$ alkyl sulfate, a trideceth sulfate, a $C_{12-13}$ pareth sulfate, a $C_{12-13}$ pareth-n sulfate, a $C_{12-14}$ pareth-n sulfate, and combinations thereof.

3. The composition of claim 1, wherein said anionic surfactant is a trideceth sulfate.

4. The composition of claim 1, wherein said betaine is an amidoalkyl betaine.

5. A personal care product comprising a composition of claim 1.

6. The personal care product of claim 5 wherein said product is selected from the group consisting of shampoos, soaps, washes, bath additives, gels, lotions, and creams suitable for use on the human body.

7. The composition of claim 1 wherein the weight ratio of branched fatty alcohol to active betaine is from about 0.15:1 to 0.35:1.

* * * * *